(12) United States Patent
Peeters et al.

(10) Patent No.: US 7,167,754 B1
(45) Date of Patent: Jan. 23, 2007

(54) LOW POWER INVERTED ALTERPHASIC STIMULATION IN A COCHLEAR IMPLANT

(75) Inventors: Stefaan Peeters, Aartselaar (BE); Filiep Vanpoucke, Huldenberg (BE)

(73) Assignee: Advanced Bionics Corporation, Valencia, CA (US)

( * ) Notice: Subject to any disclaimer, the term of this patent is extended or adjusted under 35 U.S.C. 154(b) by 149 days.

(21) Appl. No.: 10/993,991

(22) Filed: Nov. 19, 2004

Related U.S. Application Data

(60) Provisional application No. 60/530,532, filed on Dec. 17, 2003.

(51) Int. Cl.
*A61N 1/32* (2006.01)

(52) U.S. Cl. .......................... 607/57; 607/70; 607/71; 607/72

(58) Field of Classification Search ............ 607/55–57, 607/70–74
See application file for complete search history.

(56) References Cited

U.S. PATENT DOCUMENTS

| | | | |
|---|---|---|---|
| 4,532,930 A | 8/1985 | Crosby et al. | |
| 4,577,641 A | 3/1986 | Hochmair et al. | |
| 4,612,934 A | 9/1986 | Borkan | |
| 5,522,865 A | 6/1996 | Schulman et al. | |
| 5,601,617 A | 2/1997 | Loeb et al. | |
| 6,181,969 B1 | 1/2001 | Gord et al. | |
| 6,219,580 B1 | 4/2001 | Faltys et al. | |
| 6,289,247 B1 | 9/2001 | Faltys et al. | |

FOREIGN PATENT DOCUMENTS

WO WO 96/34508 A1 10/1996

*Primary Examiner*—Robert Pezzuto
*Assistant Examiner*—Shevon Johnson
(74) *Attorney, Agent, or Firm*—Bryant R. Gold; Victoria A. Poissant

(57) ABSTRACT

An alterphasic inverting stimulation strategy for use with a multichannel cochlear implant system consumes less power than similar strategies, yet provides better sound quality. The alterphasic inverting strategy is a strategy wherein stimulation pulses are strictly sequential, and wherein the timing and polarity of the channels is chosen such that positive and negative pulses are alternating in time in accordance with a defined pattern that staggers application of the pulses spatially across all the channels and inverts the polarity of pulses that are near each other either spatially or in time.

12 Claims, 12 Drawing Sheets

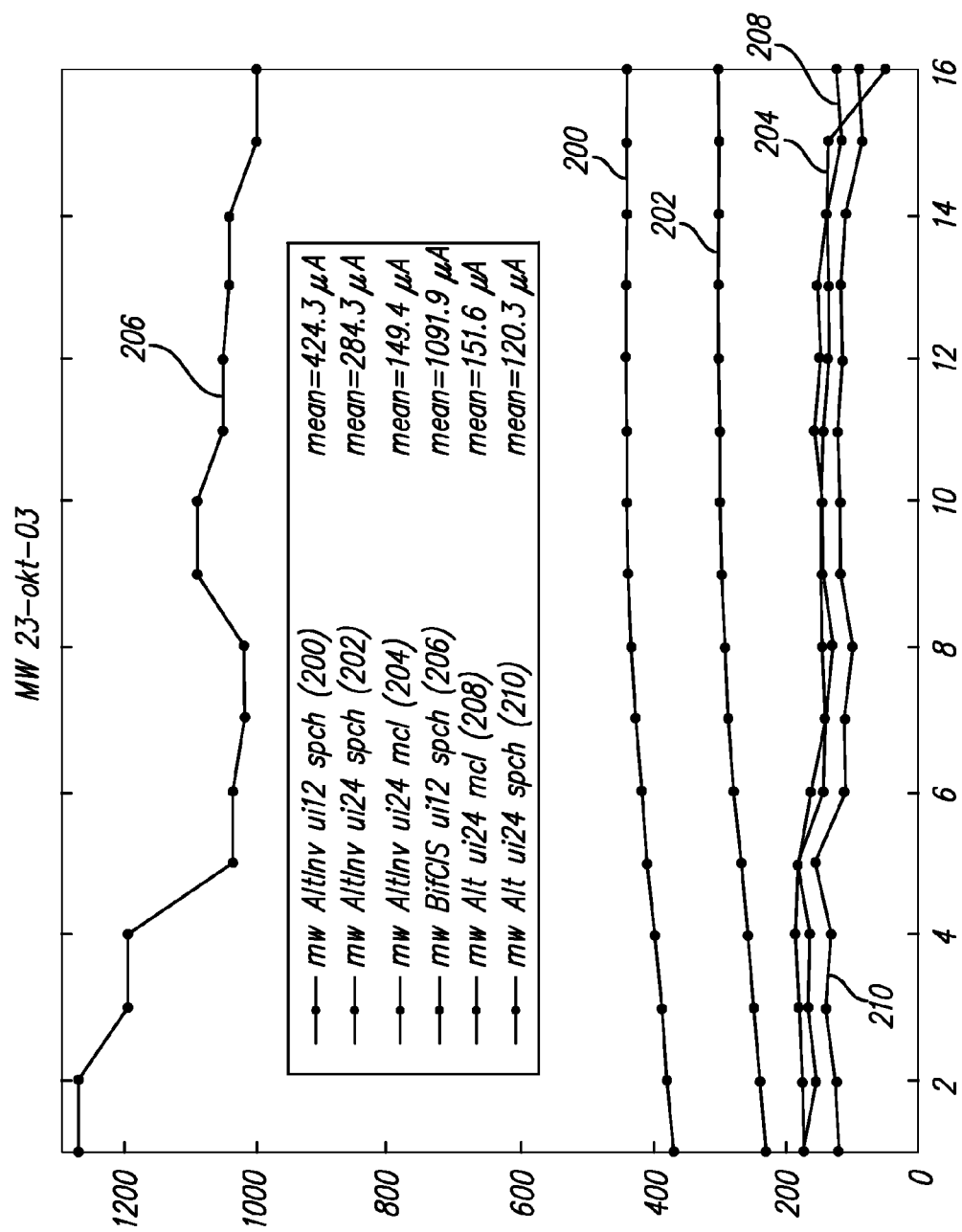

LOW POWER INVERTED ALTERPHASIC STIMULATION IN A COCHLEAR IMPLANT

The present application claims the benefit of U.S. Provisional Patent Application Ser. No. 60/530,532, filed Dec. 17, 2003, which application is incorporated herein by reference.

BACKGROUND OF THE INVENTION

The present invention relates to cochlear implants, and more particularly to a low power inverted alterphasic stimulation strategy that requires very little power to deliver good sound performance.

In U.S. Pat. No. 6,219,580, there is disclosed a multichannel cochlear prosthesis with flexible control of the stimulus waveforms. Such flexible control allows almost any stimulation waveform imaginable to be created using simple programming techniques. The U.S. Pat. No. 6,219,580 is incorporated herein by reference.

In U.S. Pat. No. 6,289,247, one technique for selecting a desired stimulation strategy from a multiplicity of stimulation strategies that may be used with a multichannel cochlear prosthesis is disclosed. The U.S. Pat. No. 6,289,247 is likewise incorporated herein by reference.

Despite the availability of stimulation prostheses and stimulation strategies of the type disclosed in the above patents, there continues to be a need to find a better stimulation strategy, i.e., a stimulation strategy that consumes less power yet delivers good sound performance.

SUMMARY OF THE INVENTION

The present disclosure addresses the above and other needs by providing an alterphasic inverting strategy that consumes less power than similar strategies, yet provides better sound quality.

The alterphasic inverting strategy of the present disclosure belongs to the family of stimulation strategies that is made possible through the use of a multichannel cochlear prosthesis of the type disclosed in the referenced patents. The referenced patents teach that an almost limitless number of stimulation strategies may be formulated and programmed into a multichannel cochlear prosthesis, bounded only by the number of channels and the ingenuity of the programmer. Some representative stimulation strategies disclosed in the referenced patents include: a continuous interleaved sampler (CIS) speech processing strategy; a paired pulsatile sampler (PPS) speech processing strategy; a simultaneous speech processing strategy, e.g., SAS; a simultaneous pulsatile sampler (SPS) strategy (wherein biphasic pulses are applied to all channels simultaneously); a hybrid analog pulsatile (HAP-4) strategy (wherein a simultaneous analog strategy is applied on four channels. and a sequential CIS-type pulsatile strategy is applied on four channels); and a multiple pulsatile sample (MPS) strategy (wherein a quad pulsatile sampler (QPS) strategy is applied in which biphasic pulses are alternately applied to four channels simultaneously). The alterphasic inverting strategy of the present disclosure is not disclosed in the referenced patents, per se, because at the time the referenced patents were filed the alterphasic inverting strategy had not been specifically identified as a possible stimulation strategy, nor had the benefits of the alterphasic inverting strategy been recognized.

The alterphasic inverting strategy of the present disclosure is a strategy wherein stimulation pulses are strictly sequential, and wherein the timing and polarity of the channels is chosen such that positive and negative pulses are alternating in time in accordance with a defined pattern.

In accordance with one aspect of the disclosure, the alterphasic inverting strategy of the present disclosure provides surprisingly good sound performance compared with other similar strategies (such as an alterphasic non-inverting strategy).

In accordance with another aspect of the disclosure, the alterphasic inverting strategy of the present disclosure requires very little power.

It is thus a feature of the present disclosure to provide a speech processing strategy that requires very little power to deliver good sound performance.

BRIEF DESCRIPTION OF THE DRAWINGS

The above and other aspects, features and advantages of the present invention will be more apparent from the following more particular description thereof, presented in conjunction with the following drawings wherein:

FIG. 8A shows the M-levels for subject MW when using the alterphasic inverting strategy of the present disclosure.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1A:
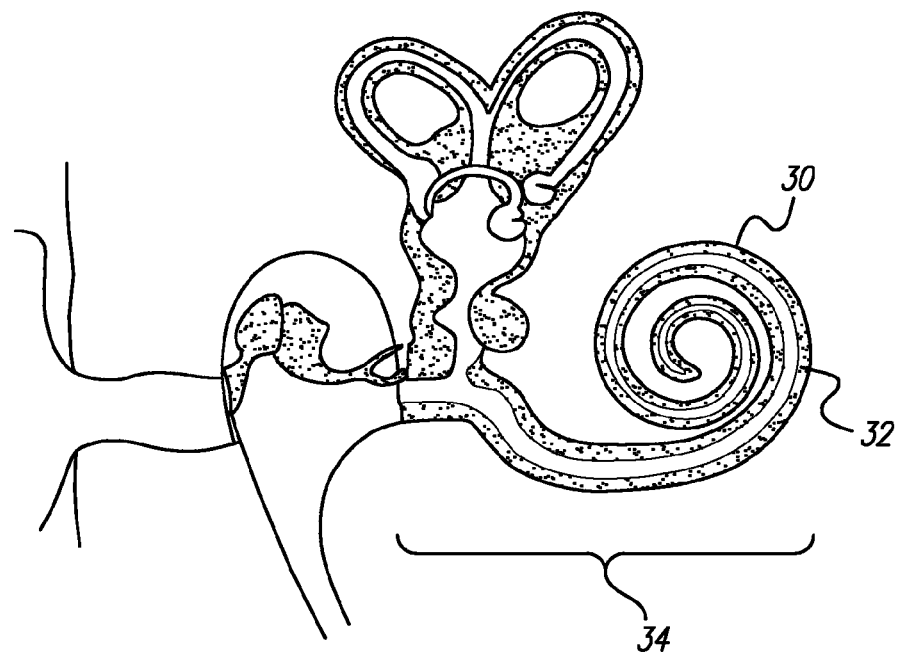
FIG. 1A is schematic diagram that teaches the structure of a human ear.

FIG. 1A schematically illustrates the structure of a human ear. For purposes of understanding the present disclosure, the parts of the human ear of most interest are the cochlea 30 and the perilymph 32. The cochlea 30 is that portion of the inner ear 34 where an electrode array 24 of a cochlear implant device 20 (shown in FIG. 2) is inserted in order to provide selective electrical stimulation of the nerves of the inner ear. The perilymph 32 is the fluid between the bony and membranous labyrinths of the ear. Many of the voltage measurements referenced hereinafter that are associated with the operation of a cochlear implant are taken in the perilymph 32 that is near certain electrodes of the electrode array within the cochlea.

Figure 1B:
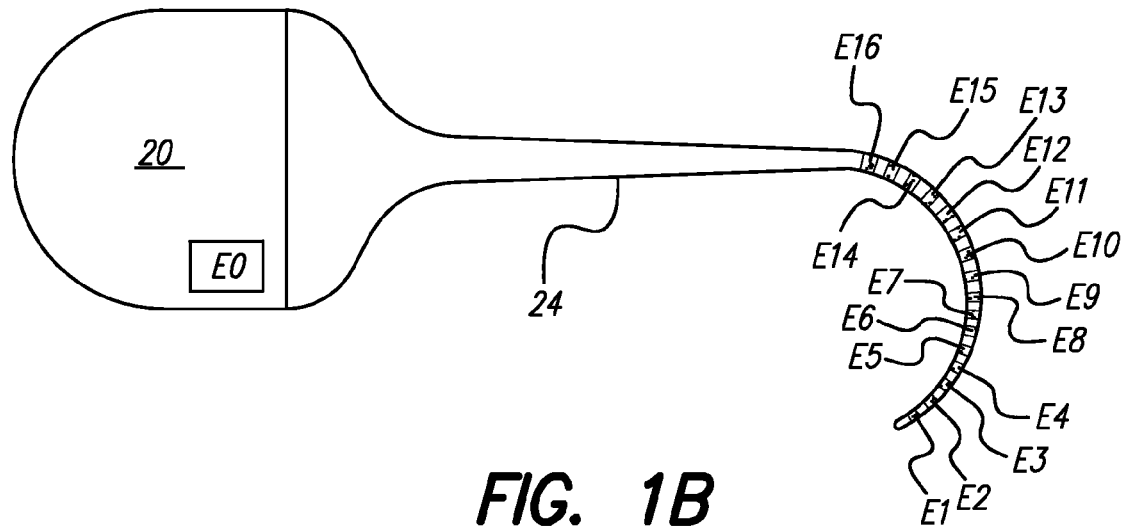
FIG. 1B illustrates a multi-channel cochlear implant system comprising an implant device and an electrode array, wherein an indifferent electrode is provided as part of the implant device, and sixteen spaced-apart electrodes, identified as electrodes E1 through E16, are provided at or near a distal end of the electrode array.

FIG. 1B illustrates the implantable components of a multi-channel cochlear implant system. These implantable components comprise an implant device 20 and an electrode array 24. An indifferent electrode E0 is typically provided on the case of the implant device 20. Sixteen spaced-apart electrode contacts, identified as electrodes E1 through E16, are provided at or near a distal end of the electrode array 24. (Sixteen is only an exemplary number of electrode contacts; there may be fewer or more than sixteen electrode contacts used in a particular electrode array.) Electrical stimuli, in the form of pulses of electrical current, are applied to the tissue surrounding selected ones of the electrodes E1 through E16 in order to excite desired nerves within the inner ear, thereby providing a user of the implant device with the sensation of hearing. The particular electrodes that are stimulated at any given time is a function of the sound signals sensed by the cochlear implant system and a selected speech processing stimulation strategy, as is described in the referenced U.S. Pat. Nos. 6,219,580 and 6,289,247.

Application of the pulses of electrical stimuli through the electrode contacts E1 through E16 may be performed using monopolar stimulation, bipolar stimulation, or multipolar stimulation. In monopolar stimulation, the pulses of electrical stimuli are applied between one of the electrode contacts and the reference, or indifferent, electrode contact E0. In bipolar stimulation, the pulses of electrical stimuli are applied between two of the electrode contacts, with one electrode contact functioning as the anode at any instant of time and the other functioning as the cathode at the same instant of time. In multipolar stimulation, the pulses of electrical stimuli are applied between a multiplicity (three of more) of the electrode contacts, with at least one electrode contact functioning as the anode at any instant of time, and with at least one other electrode contact functioning as the cathode at the same instant of time. A preferred technique for application of the electrical stimuli to selected ones of the electrode contacts is to use current sources associated with each electrode contact that are configured to "source" or "sink" a programmed amount of current, as described in U.S. Pat. No. 6,181,969, incorporated herein by reference.

For purposes of the Inverted Alterphasic Stimulation technique of the present disclosure, as explained more fully below, the pulses of electrical stimuli are applied monopolarly and sequentially to just one electrode at any instant of time. Such sequential stimulation offers the advantage of lower power consumption as it is carried out than do other forms of stimulation, such as stimulation strategies where pulses of electrical stimuli are applied to more than one electrode at the same instant of time.

Figure 2A:
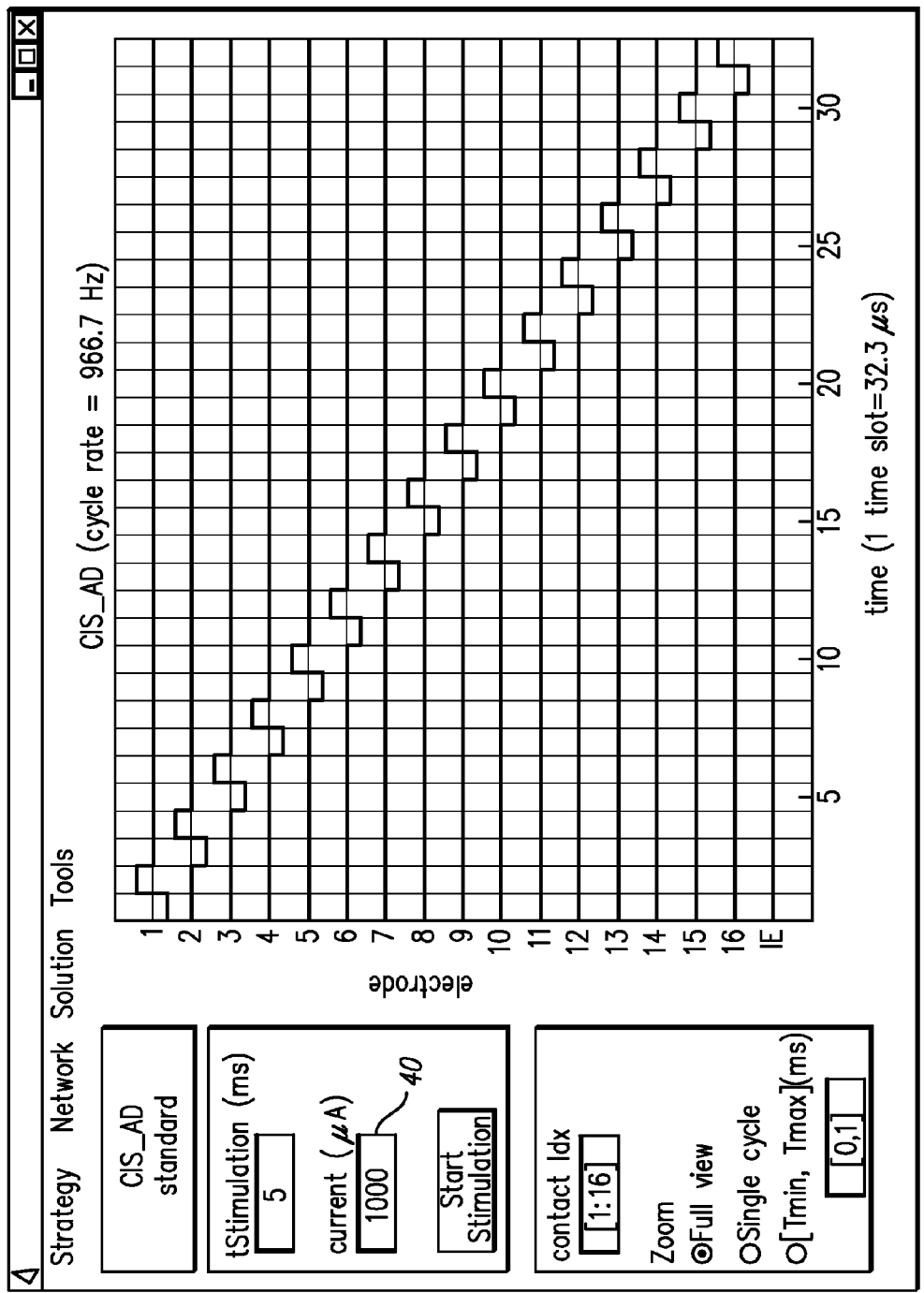
FIG. 2A illustrates, for comparative purposes, the application of biphasic pulses in accordance with a CIS strategy on 16 sequential channels.

FIG. 2A illustrates, for comparative purposes, the application of biphasic pulses in accordance with a CIS strategy on 16 sequential channels. A "biphasic" pulse is one having a first pulse of one polarity, followed by a second pulse of the same magnitude of the opposite polarity. In contrast, a single pulse of one polarity is referred to as a "monophasic" pulse. Thus, a biphasic pulse is made up of two monophasic pulses. Where there is a time gap inserted between the first pulse of one polarity and the second pulse of the opposite polarity, a quasi biphasic pulse results, which for purposes of the present disclosure is referred to as an "alterphasic" pulse.

That which is shown is FIG. 2A is one of the display screens used as part of a programming system of a cochlear implant system as described more fully, e.g., in U.S. Pat. No. 6,289,247, previously referenced. It shows the type of stimulus pulse that is applied to each electrode contact as a function of time. The amplitude of the stimulus pulse is as specified in the programming window 40 to the left of the waveform display. For the example shown, the programmed current pulse amplitude is 1 milliamp (ma) or 1000 microamps ($\beta$A).

As seen in FIG. 2A, electrode contact E1, the first line in the waveform display, has a biphasic pulse applied to it, comprising a negative pulse having a 1 ma amplitude and a duration of 32.3 microseconds ($\mu$s) followed immediately (without delay) by a positive pulse having a 1 ma amplitude and a duration of 32.3 $\mu$s. As soon as the biphasic pulse applied to electrode contact E1 has concluded, a biphasic pulse having the same characteristics (1 ma amplitude, 32.3 $\mu$s per pulse duration, or a 64.7 $\mu$s biphasic pulse total duration) is applied to electrode contact E2. In a similar fashion, as soon as the biphasic pulse applied to electrode contact E2 has concluded, a biphasic pulse is applied to electrode contact E3, then when finished to electrode contact E4, and so on, through all sixteen electrode contacts. The biphasic pulses are applied sequentially, with only one electrode having a pulse applied to it at any instant of time.

Figure 2B:
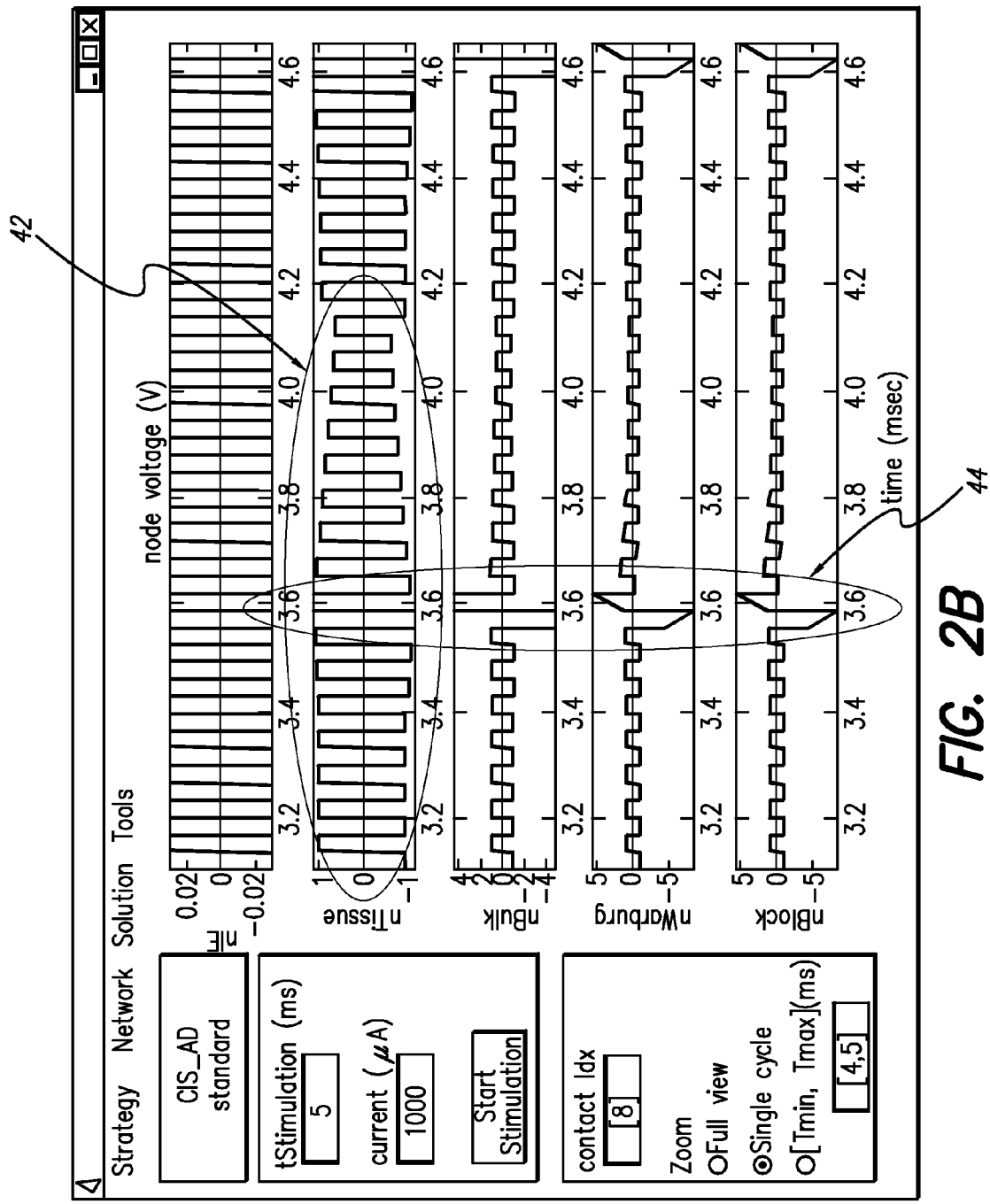
FIG. 2B shows the voltage waveforms measured at electrode E8 associated with the biphasic CIS stimulation of FIG. 2A.

FIG. 2B shows various voltage waveforms measured at electrode E8 associated with the biphasic CIS stimulation of FIG. 2A. The most relevant voltage waveform for purposes of the present discussion is the second waveform from the top (encircled by the horizontal ellipse 42). The other waveforms shown in FIG. 2B are measured at different locations throughout the circuitry that provides the stimulation. For example, the top waveform is the voltage waveform as measured at the indifferent electrode contact E0. The third waveform from the top is measured at a bulk resistor, the fourth waveform from the top at a particular capacitor, and the bottom waveform at the coupling capacitor. The vertical ellipse 44 highlights the time when electrode contact E8 is simulating. Clearly, all sixteen biphasic pulses are observed at electrode contact E8 due to the electrical coupling known from EFI.

FIG. 3A illustrates, again for comparative purposes, the application of an alterphasic non-inverting strategy on 16 channels. The alterphasic non-inverting strategy shown in FIG. 3A comprises a type of alternating phase strategy wherein pulses are strictly sequential. The negative pulses of all channels are scheduled in the first half of the pulse table. Channels are staggered for maximal separation in space between consecutive channels. Every negative pulse is preceded by a single phase in which the respective electrode contact is grounded to eliminate potential charge imbalance. (For speed reasons, discharge phases are paired.) The positive pulses are grouped in the second half.

Figure 3A:
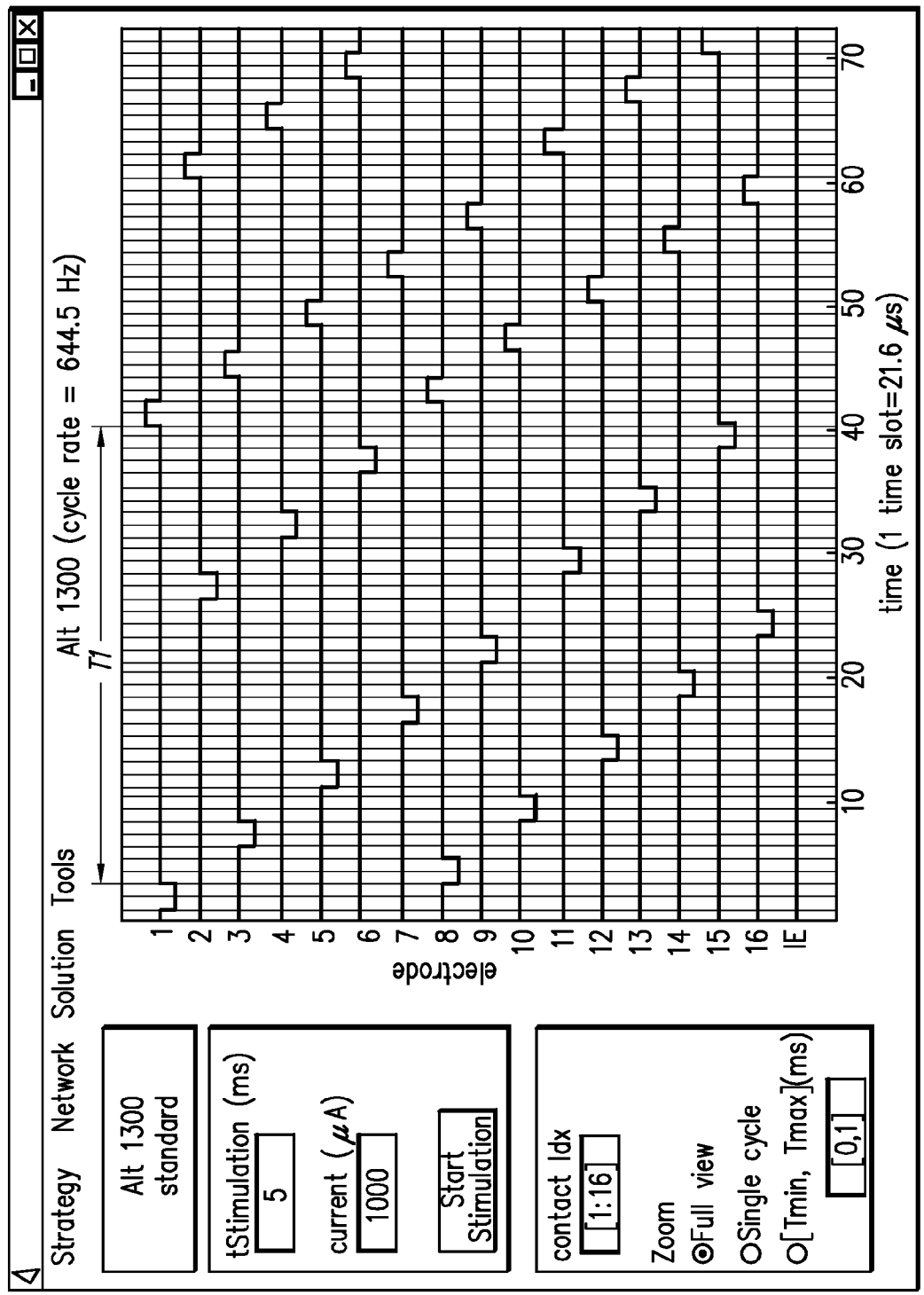
FIG. 3A illustrates, again for comparative purposes, the application of an alterphasic non-inverting strategy on 16 channels.

Another way to describe the alterphasic non-inverting strategy shown in FIG. 3A is that alterphasic pulses are applied sequentially to each of the sixteen channels in a prescribed sequence that staggers the stimuli for maximal separation in space. Each alterphasic pulse comprises a negative pulse, a long delay (or time gap) of T1 seconds, and a positive pulse. In order to stagger the stimulation applied to each channel in space by a maximum amount, the following stimulation sequence is used: E1, E8, E3, E10, E5, E12, E7, E14, E9, E16, E2, E11, E4, E13, E6, E15. Other stimulation sequences could also be used that would provide a similar staggered-in-space result. As seen in FIG. 3A, all of the negative pulses of the alterphasic pulses appear in the first half (left half) of the pulse table, while all of the positive pulses of the alterphasic pulses appear in the second half (right half) of the pulse table.

Figure 3B:
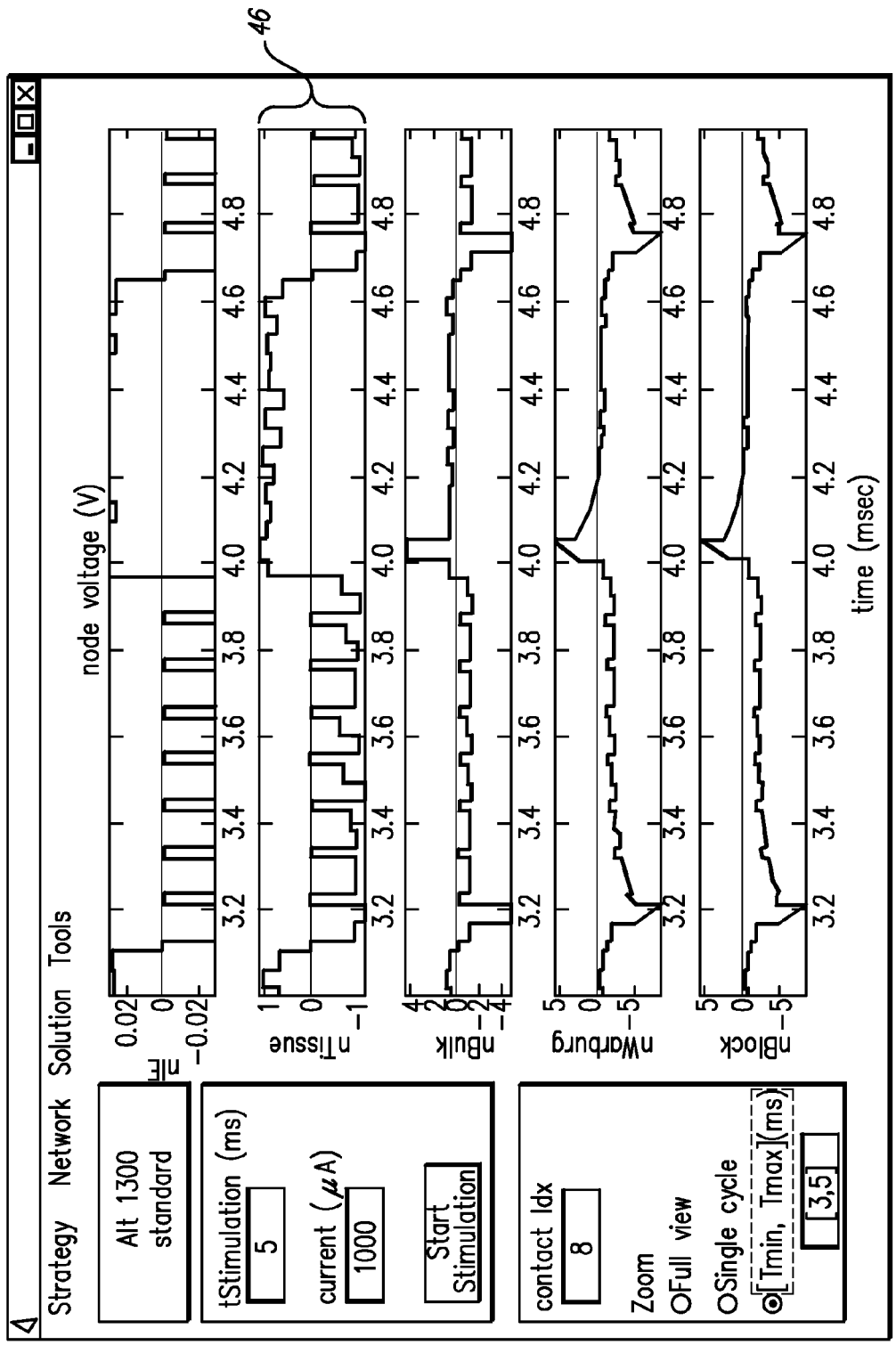
FIG. 3B shows the voltage waveforms measured at electrode E8 associated with the alterphasic non-inverting strategy of FIG. 3A.

FIG. 3B shows the voltage waveforms measured at electrode E8 associated with the alterphasic non-inverting strategy of FIG. 3A. The most relevant voltage waveform for purposes of the present discussion is the second waveform 46 from the top, and comprises the voltage in the perilymph near electrode contact E8. The other waveforms shown in FIG. 3B are measured at different locations throughout the electrical circuitry that provides the stimulation, similar to what was shown in FIG. 2B.

As can be seen from FIG. 3B, a very broad pulse is observed at electrode contact E8. The positive phases of all channels more or less sum together to create a single pulse with some amplitude dither. The negative pulses contain some zero phases due to the presence of the grounding phases. Disadvantageously, a neuron in the cochlea in the neighborhood of electrode contact E8 is likely to react on the broad pulse instead of the individual pulses, thereby giving rise to a distorted speech perception.

Figure 4:
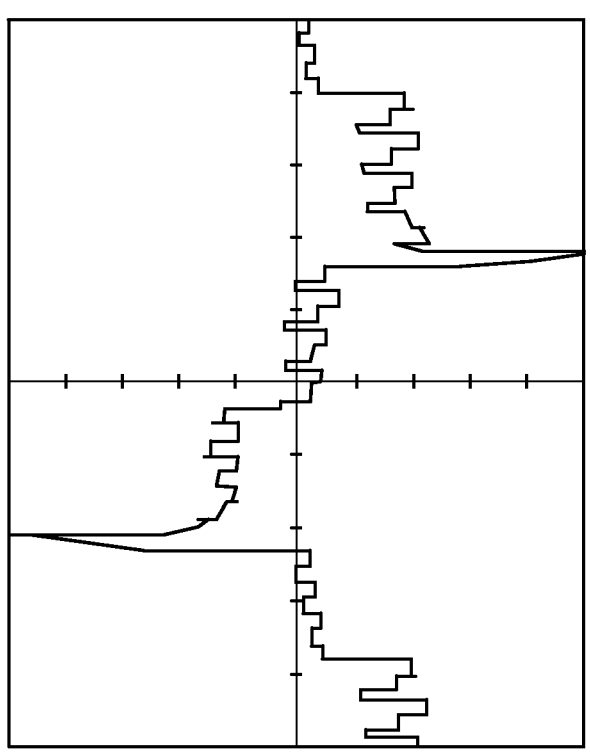
FIG. 4 shows the voltage measured in the perilymph at electrode contacts E1 and E14 associated with application of the alterphasic non-inverting strategy of FIG. 3A, and illustrates that such application causes the nerves to see a large low frequency biphasic pulse modulated with monophasic pulses.
Figure 4:
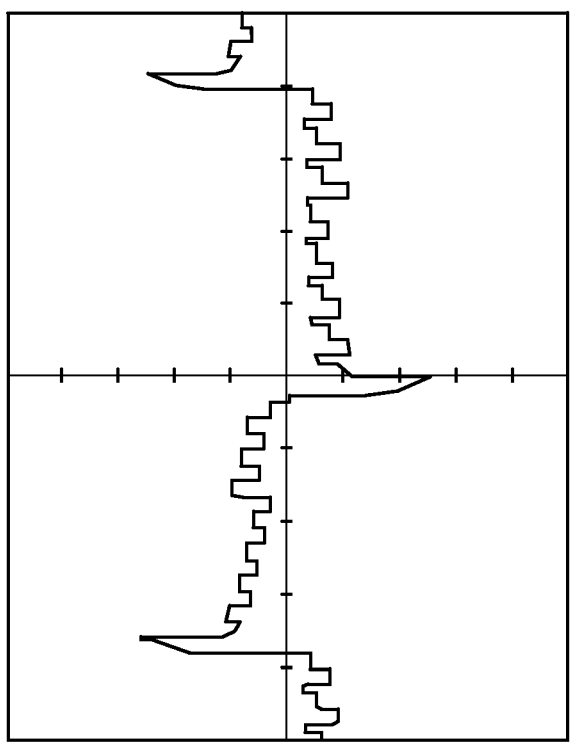

FIG. 4 shows the voltage measured in the perilymph at electrode contact E1 (on the left) and electrode contact E14 (on the right) associated with application of the alterphasic non-inverting strategy of FIG. 3A. As can be seen from FIG. 4, the application of the alterphasic non-inverting strategy causes the nerves to see a large low frequency biphasic pulse modulated with monophasic pulses. The large pulse results in an extra lowering of the stimulation level when speech stimulation is provided with the large pulse, but disadvantageously appears to be responsible for poor speech understanding.

Figure 5:
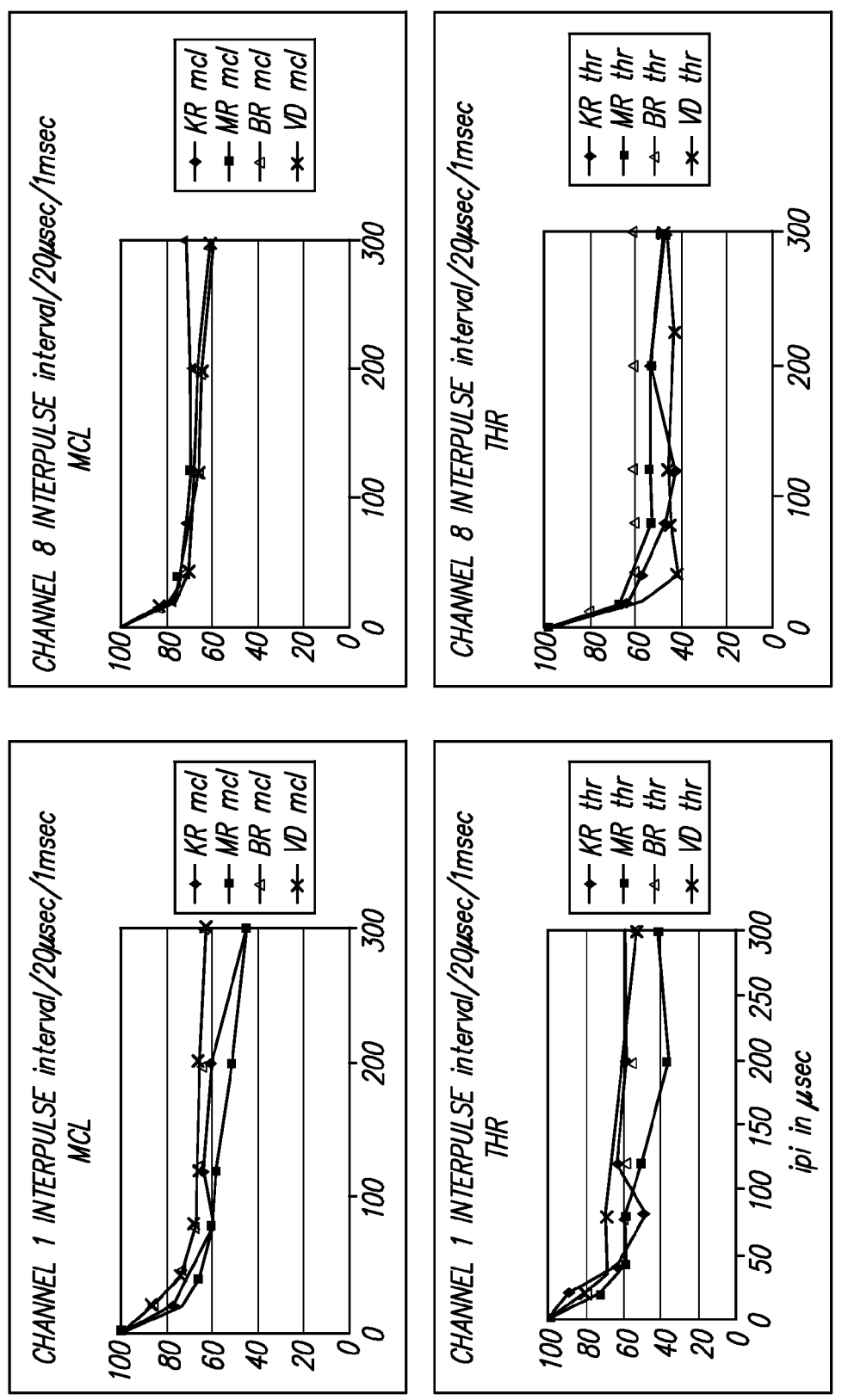
FIG. 5 shows graphs that help illustrate that the nerve reacts more efficiently when a time gap is inserted between the two phases of a biphasic pulse.

FIG. 5 shows graphs that help illustrate that the nerve appears to react more efficiently when a time gap, such as the time gap T1 (shown in FIG. 3A), is inserted between the two phases of a quasi biphasic pulse, or an alterphasic pulse. An experiment was conducted on two subjects (patients) in which the time gap was increased from 0 µs to 100 µs. These channels were then mapped. The resulting fittings, shown in FIG. 5, show that there is a clear decrease on the M-levels by a factor of "y" over a time gap increase up to "z" µs. The M-level, explained more fully in the previously referenced U.S. Pat. No. 6,289,247, is the stimulation amplitude for a given channel that is perceived by the subject as being most comfortable. It is important, of course, that the subject be able to perceive the stimulation applied on any given channel, and that such stimulation be "comfortable" (not too loud, but not too soft). The M-levels thus form an important parameter when programming a given cochlear implant system to fit the needs of a particular subject. The lower the M-levels, the lower the power consumption of the implant system. Thus, the experiments conducted appear to confirm that M-levels can be reduced, and hence less power will be used, by using alterphasic stimulation, i.e., by inserting a time gap between sequentially-applied monophasic pules having alternating polarity.

Figure 6A:
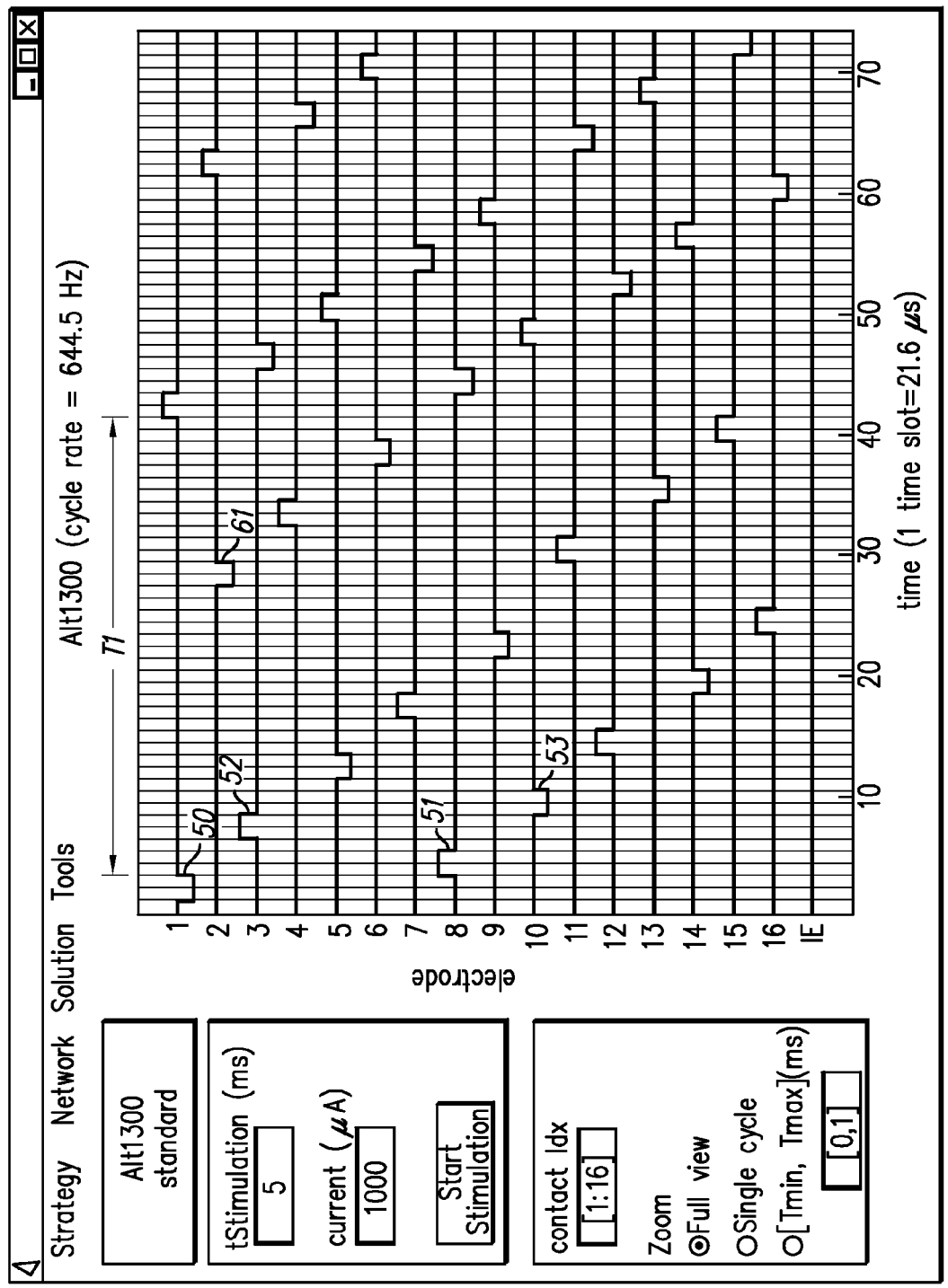
FIG. 6A illustrates the application of an alterphasic inverting strategy on 16 channels in accordance with the present disclosure.

Next, with reference to FIG. 6A, there is illustrated the application of an alterphasic inverting strategy on 16 channels in accordance with the present disclosure. The alterphasic inverting strategy shown in FIG. 6A differs from the alterphasic non-inverting strategy shown in FIG. 3A in that in half of the channels the polarity of the alterphasic pulse is reversed. The timing and polarity of the channels is selected such that positive and negative pulses are, more or less, alternating in time. The selected channel stimulation sequence for the alterphasic inverting strategy shown in FIG. 6A is:

E1(−), E8(+), E3(+), E10(−), E5(−), E12(+), E7(+), E14(−), E9(−), E16(+), E2(−), E11(+), E4(+), E13(−), E6(−), E15(+), . . . ;

where the polarity symbol in parenthesis indicates the polarity of the first pulse of the alterphasic pulse applied to that channel, and where a time gap of T1 seconds is inserted between the two pulses of the alterphasic pulse, as shown in FIG. 6A.

Figure 6B:
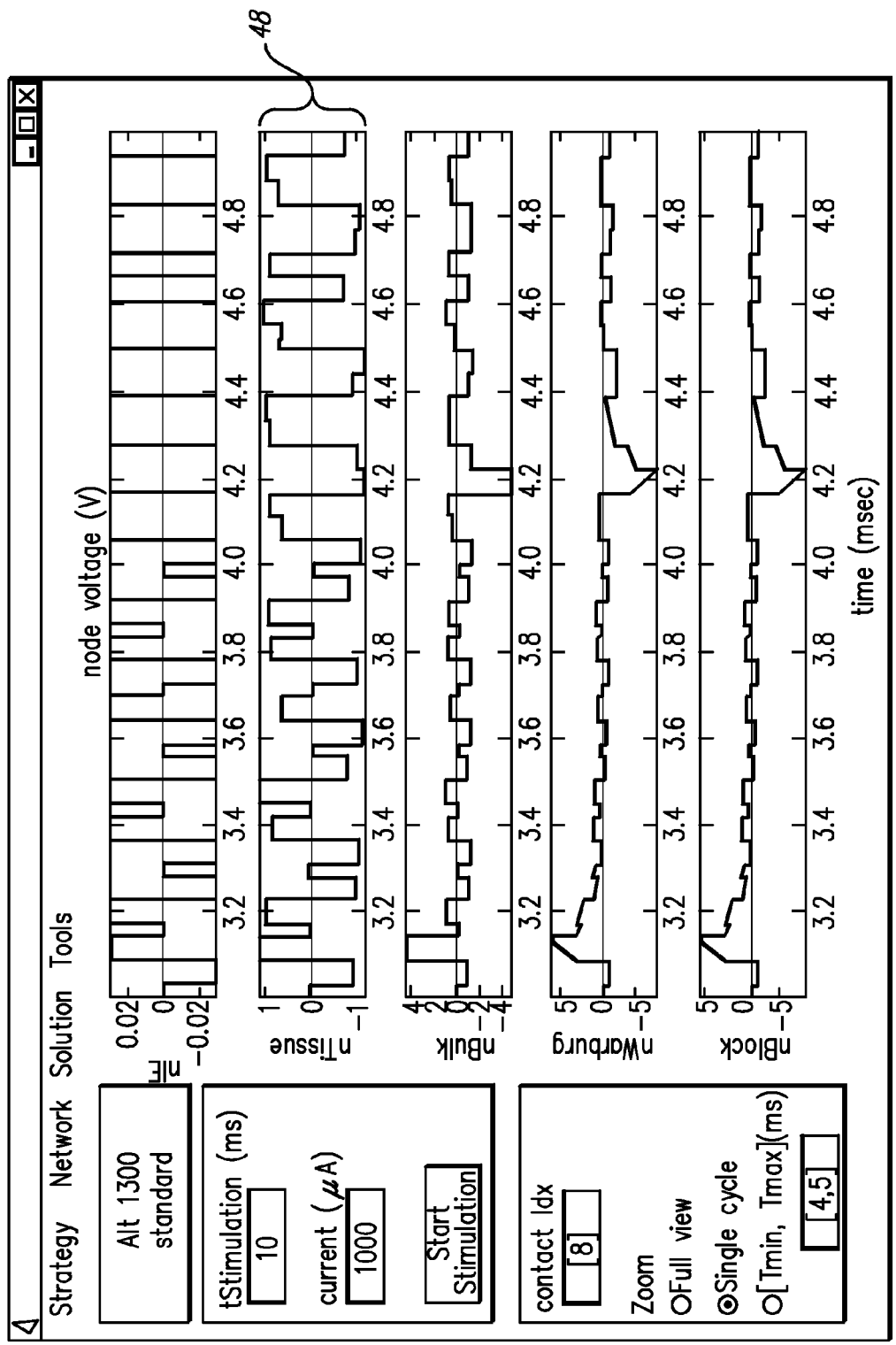
FIG. 6B shows the voltage waveforms measured at electrode E8 associated with the alterphasic inverting strategy of FIG. 6A.

FIG. 6B shows the voltage waveforms measured at electrode E8 associated with the alterphasic inverting strategy of FIG. 6A. The most relevant voltage waveform for purposes of the present discussion is the second waveform from the top, and comprises the voltage in the perilymph near electrode contact E8. The other waveforms shown in FIG. 6B are measured at different locations throughout the circuitry that provides the stimulation, similar to what was shown in FIG. 2B. As can be seen from FIG. 6B, the different polarity of the channels used by the alterphasic inverting strategy has a profound impact on the time evolution of the intracochlear potentials. More particularly, as is seen in FIG. 6B, the voltage in the perilymph may be interpreted as a sequence of unbalanced biphasic pulses.

Figure 7:
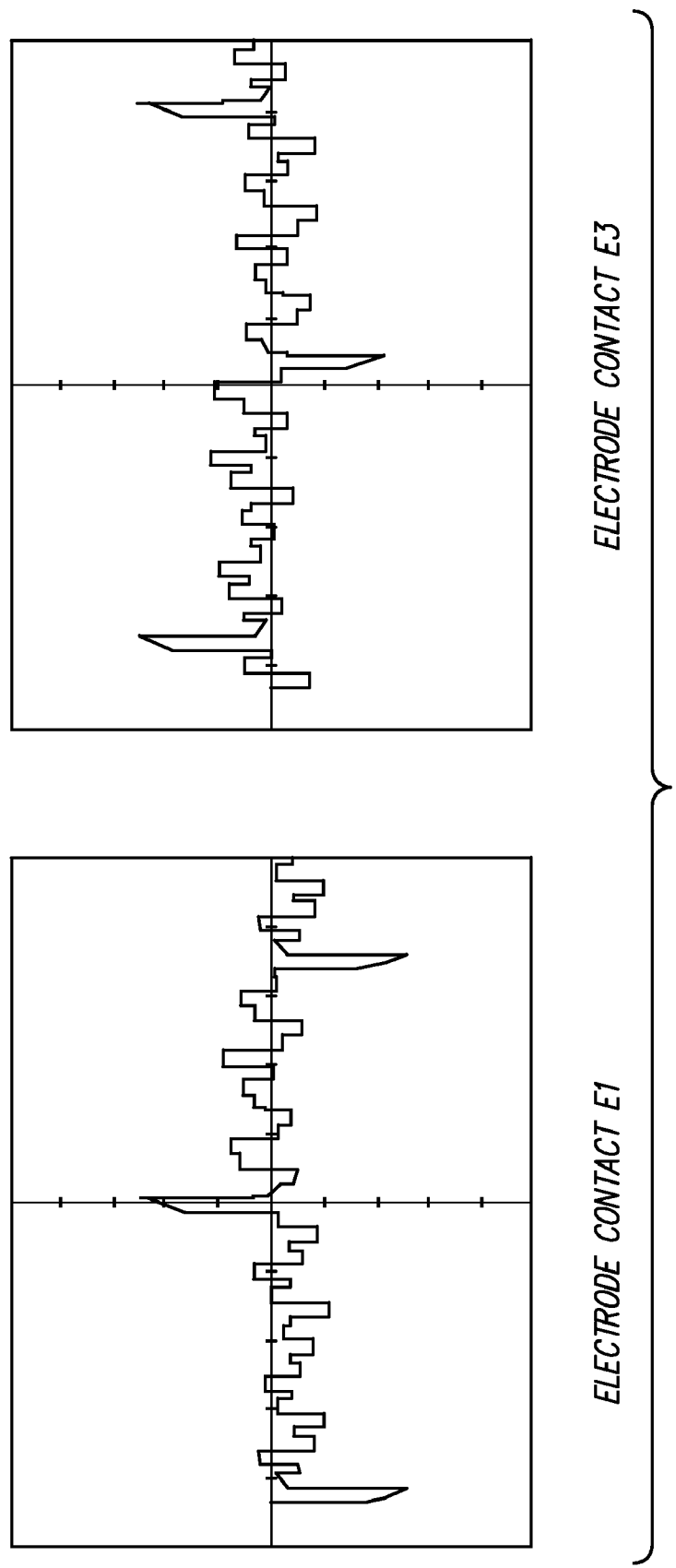
FIG. 7 shows the voltage measured in the perilymph at electrode contacts E1 and E3 associated with application of the alterphasic inverting strategy of FIG. 6A, and illustrates that such application causes the nerves to see an alternating voltage aligned with the monophasic alternating-in-polarity pulses of the alterphasic inverting strategy, and further illustrates that the large low frequency biphasic pulse seen in FIG. 4 has disappeared.

FIG. 7 shows the voltage measured in the perilymph at electrode contacts E1 (left) and E3 (right) associated with application of the alterphasic inverting strategy of FIG. 6A. Significantly, FIG. 7 illustrates that application of the such strategy causes the nerves to see an alternating voltage aligned with the monophasic alternating-in-polarity pulses of the alterphasic inverting strategy. Advantageously, FIG. 7 further illustrates that the large low frequency biphasic pulse seen in FIG. 4 has disappeared.

Advantageously, when using the alterphasic inverting strategy as shown in FIG. 6A, or an equivalent alterphasic inverting strategy (see next paragraph), the perceived speech quality and performance of a subject using such strategy increases. This fact potentially has a huge consequence on the manner in which speech algorithms are developed. This is because the whole voltage pattern in the perilymph appears to play an important and critical role in ability of the subject (patient) to perceive and understand sound, as well as to discriminate good sound quality from poor sound quality.

Note that the sequence of channel stimulation indicated above and in FIG. 6A is not the only sequence that could be used to practice the alterphasic inverting stimulation strategy of the present disclosure. The sequence shown in FIG. 6A is as follows:

E1(−), E8(+), E3(+), E10(−), E5(−), E12(+), E7(+), E14(−), E9 (−), E16(+), E2(−), E11(+), E4(+), E13(−), E6(−), E15(+), . . . ;

where the polarity symbol in parenthesis indicates the polarity of the first pulse of the alterphasic pulse applied to that channel, and where a time gap of T1 seconds is inserted between the two pulses of the alterphasic pulse, as shown in FIG. 6A. However, this sequence of stimulation is only exemplary. Any stimulation strategy could be used where the dual goals of inverting the polarity of the pulses and staggering the pulses so as to maximize the separation distance between adjacent-in-time pulses are achieved. In FIG. 6A, for example, it is seen that the first monophasic pulse 50 is a negative pulse applied through electrode contact E1, and the next-in-time pulse that is applied is a positive monophasic pulse 51 applied through electrode contact E8, a contact that is physically separated from contact E1 by a large distance. The next-in-time pulse that is applied after the positive pulse 51 is applied through contact E8 is another positive pulse 52 that is applied through electrode contact E3. The next-in-time pulse is negative pulse 53 applied through contact E10. This pulse 52 is quite close spatially, as well as in time, to the negative pulse 50 that was applied through contact E1, hence pulse 52 is selected to be of a polarity that is opposite from that of the pulse 50 applied through contact E1. In contrast, the pulse 52 is spatially separated from the more recent-in-time pulse 51 that was applied through electrode contact E8; thus pulse 52 is of the same polarity as pulse 51 applied through electrode contact E8.

Thus, as a stimulation sequence is selected for providing stimulation pulses in accordance with the alterphasic inverting stimulation strategy of the present disclosure, the following criteria should be considered: (a) alterphasic pulses are applied to each channel that is to be used, but the monophasic pulses that make up the alterphasic pulse are separated by a time gap T1 (FIG. 6A) that is quite large; (b) stimulation pulses are applied sequentially, such that only one monophasic pulse is present at any given time; (c) monophasic pulses that are close to each other in time and in space should be inverted in polarity; and (d) monophasic pulses that are close to each other in time, but not close to each other spatially, may be of the same polarity. When these criteria are followed, then the voltage pattern seen in the perilymph will be an alternating pattern, and no large low frequency biphasic pulses will be present.

A significant advantage realized through use of the alterphasic inverting stimulation strategy of the present disclosure is a reduction in power associated with operation of the cochlear implant system. Such reduction in power results from the sequential nature of the pulses that are applied, and from the decreased M-levels which result from the inverting nature of such pulses which prevents any large low frequency pulses to be present. The inverting strategy also appears to significantly improve the ability of the user to perceive sound, as well as to improve the ability of the user to discern quality of sound.

As an approximate power consumption metric, it may be assumed that the consumed power is roughly proportional to the average M-level squared times the duty cycle, or $$\text{Power} \propto (\text{Average M level})^2 \times \text{duty cycle}.$$

This quadratic relation results because the supply voltage can be proportionally lowered if the peak current is decreased. The duty cycle is the absolute value of the current sources averaged over all phases. Since all three strategies, biphasic (FIG. 2A); alterphasic non-inverting (FIG. 3A); and alterphasic inverting (FIG. 6A) roughly have a unity duty cycle, the duty cycle factor can be discarded.

Figure 8B:
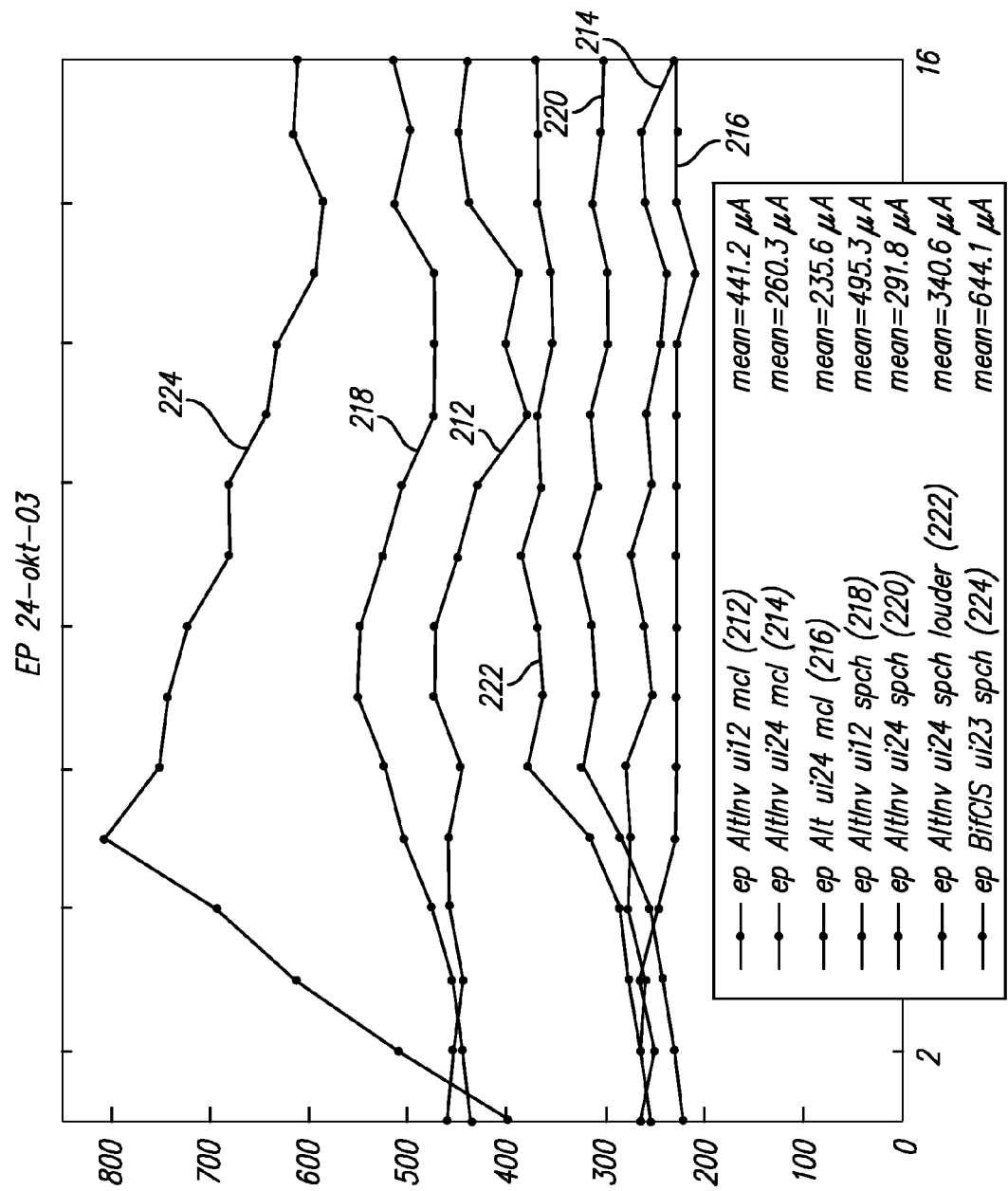
FIG. 8B similarly shows the M-levels for subject EP when using the alterphasic inverting strategy of the present disclosure.

To test the present disclosure, two subjects (patients) were fitted with a subset of the following strategies: (1) alternating non-inverting strategy at 20 µs pulse width and 40 µs phase width; and (2) alternating inverting strategy at 20 µs pulse width and 40 µs phase width. These fittings were compared to the setting for the subjects' baseline fitting program obtained using a conventional fitting approach (e..g, Soundwave at 20 µs). Only M-levels were determined, and T-levels were kept at zero. The obtained M-levels were also compared with pure tones (MCL) and speech (SPCH). The resulting M-level curves obtained from the two subjects are shown in FIGS. 8A and 8B, respectively.

Table 1 provides some relevant comparisons obtained from subject "MW" and subject "EP" based on the mean M-level parameters

TABLE 1

Mean M-Levels

| COMPARISON | Subject MW | Subject EP |
|---|---|---|
| ALTINV vs ALT | SPCH: 284 vs 120 (−58%)<br>MCL: 140 vs. 152 | 260 vs 236 (−10%) |
| UI 24 vs 12 | 284 vs 424 (+50%) | 292 vs 495 (+70%) |
| BIPHASIC vs ALTINV (@22 µs) | 546 vs 424 (−22%) | 644 vs 495 (−23%) |

Row 1 of Table 1 shows a surprising result for the alterphasic non-inverting strategy (ALT). When fitting with pure tones, the M levels for inverting and non-inverting strategies lie very close together. Only a single channel is activated and therefore the neural responses are identical, independent of the polarity of the first phase. However, when playing speech, the M-level needs to be decreased for subject MW from 152 µs to 120 µs for the non-inverting strategy, whereas for the inverting case, the M-levels can be increased beyond the comfortable level. This is a clear indication that the nerve now reacts to the composed broad pulse. For subject EP the difference is less pronounced.

Row 2 of Table 1 compares the levels between 40 µs and 20 us. The increase in stimulation current is substantially less than the expected factor of 2. This suggests that the nerve can react on the positive and negative pulse partially independently.

Finally, row 3 of Table 1 indicates that the ALTINV strategy results in a 20% decrease of the M-levels. Thus, it appears that its quasi-biphasic nature is still more efficient than an instantaneous biphasic pulse with 100% instantaneous charge reversal.

FIG. 8A shows the M-levels for subject MW when using the alterphasic inverting strategy of the present disclosure. It is noted that the reference numerals 200, 202, 204, 206, 208, and 210 shown in FIG. 8A are used to identify appropriate plots of M-levels for subject MW as defined in the table portion of FIG. 8A.

FIG. 8B similarly shows the M-levels for subject EP when using the alterphasic inverting strategy of the present disclosure. It is noted that the reference numerals 212, 214, 216, 218, 220, 222, and 224 shown in FIG. 8B are used to identify appropriate plots of M-levels for subject EP as defined in the table portion of FIG. 8B.

As seen from the above description, the present disclosure may be characterized as a method for sequentially stimulating the cochlea of a subject. Such method comprises the following steps:

(1) inserting an electrode array into the cochlea, wherein the electrode array has a multiplicity of spaced-apart electrode contacts on it that, when the electrode array is fully inserted into the cochlea, are positioned spatially along the length of the cochlea;

(2) stimulating a first electrode contact on the electrode array with a monophasic pulse having a first polarity;

(3) stimulating a second electrode contact on the electrode array immediately following (or after a short delay from) stimulation of the first electrode contact with a monophasic pulse having a second polarity, wherein the second polarity (a) is the opposite polarity of the pulse applied to the first electrode contact whenever the second electrode contact is spatially near the first electrode contact, and (b) the same polarity or the opposite polarity of the pulse applied to the first electrode contact whenever the second electrode contact is spatially far from the first electrode contact;

(4) stimulating a third electrode contact on the electrode array immediately following (or after a short delay from) stimulation of the second electrode contact with a monophasic pulse having a third polarity, wherein the third polarity (a) is the opposite polarity of the pulse applied to the second electrode contact whenever the third electrode contact is spatially near the second electrode contact, and (b) is the same polarity or the opposite polarity of the pulse applied to the second electrode contact whenever the third electrode contact is spatially far from the second electrode contact;

(5) continuing to stimulate electrode contacts on the electrode array following the above pattern until a desired number of electrode contacts have been stimulated;

(6) repeating the above stimulation pattern for all of the electrode contacts on the electrode array stimulated by a monophasic pulse of one polarity by stimulating that electrode contact with a monophasic pulse of an opposite polarity, whereby a selected number of the electrode contacts on the electrode array are stimulated in accordance with an alterphasic inverting stimulation strategy; and (7) modulating the alterphasic inverting stimulation with sound information.

In the description of the above method, the terms "spatially far" and "spatially near" are used. These are terms that are meant to be relative with respect to both the time at which a given pulse is applied to a specified electrode contact with respect to the time when other pulses are applied to other specified electrode contacts, and with respect to the physical distance the electrode contacts are separated on the electrode array. For example, with respect to FIG. 6A, the positive monophasic pulse 52 is considered to be close in time and spatially near the negative monophasic pulse 50 because electrode contact E3—the electrode contact on which the pulse 52 is applied—is near electrode contact E1—the electrode contact on which the pulse 50 is applied. Moreover, pulse 52 is applied to electrode contact E3 close in time to when pulse 50 is applied to electrode contact E1—only about 32 μs after pulse 50 is applied to contact E1. A pulse applied to one electrode contact will always be considered to be "spatially near" a previously-applied pulse to another electrode contact if the two electrode contacts are physically close to each other, e.g., adjacent to each other or only having a one or two electrode contact separation, and if the two pulses are applied close in time to each other, e.g., within the time gap between the pulses is less than or equal to two times the pulse width.

In contrast, the positive monophasic pulse 51 is considered to be "spatially far" from the negative monophasic pulse 50 because electrode contact E8—the electrode contact on which the pulse 51 is applied—is far from electrode contact E1—the electrode contact on which the pulse 50 is applied—because there are six electrode contacts that separate electrode contact E1 from electrode contact E8. Electrode contact E8 is considered spatially far from electrode contact E1 even though the pulse 51 is applied to electrode contact E8 immediately after the pulse 50 is applied to electrode contact E1; that is, even though pulse 51 is applied close in time to the application of pulse 50.

It should be noted, however, that physical proximity of two electrode contacts does not assure that the pulses applied to those contacts will be considered as "spatially near" each other. For example, in FIG. 6A, the pulse 61 applied to electrode contact E2, which is adjacent electrode contact E1, and thus physically near electrode contact E1, is considered to be "spatially far" from the pulse 50 applied to electrode contact E1 because pulse 61 is applied a long time—approximately 497 μs—after the pulse 50 is applied to electrode contact E1.

Once an alterphasic inverting stimulation pattern has been generated using the above-described method, or an equivalent method, such pattern is modulated in an appropriate manner with sound information. Such sound information may be sensed using, e.g., an external microphone, and the sound signals generated by the microphone may then be processed so as to amplitude modulate the alterphasic inverting pulses that are applied sequentially to the electrodes of the electrode array. Because the cochlea is arranged tonotopically, e.g., where neurons near the base of the cochlea respond to high frequency sound signals, and where the neurons closer to the apex of the cochlea respond to lower frequency signals, one form of modulation that may be used with the present disclosure separates the incoming sound signals into frequency bands. Once thus separated, the signal strength in each frequency band is used to modulate the intensity (amplitude) of the stimuli that are applied to respective electrode contacts corresponding to the frequency band.

While the invention herein disclosed has been described by means of specific embodiments and applications thereof, numerous modifications and variations could be made thereto by those skilled in the art without departing from the scope of the invention set forth in the claims.

What is claimed is:

1. A method for sequentially stimulating the cochlea of a subject comprising:

inserting an electrode array into the cochlea, the electrode array having a multiplicity of spaced-apart electrode contacts that are positioned spatially along the length of the cochlea;

stimulating a first electrode contact on the electrode array with a monophasic pulse having a first polarity;

stimulating a second electrode contact on the electrode array following stimulation of the first electrode contact with a monophasic pulse having a second polarity, wherein the second polarity is the opposite polarity of the pulse applied to the first electrode contact whenever the second electrode contact is spatially near the first electrode contact, and wherein the second polarity is the same polarity or the opposite polarity of the pulse applied to the first electrode contact whenever the second electrode contact is spatially far from the first electrode contact;

stimulating a third electrode contact on the electrode array following stimulation of the second electrode contact with a monophasic pulse having a third polarity, wherein the third polarity is the opposite polarity of the pulse applied to the second electrode contact whenever the third electrode contact is spatially near the second electrode contact, and wherein the third polarity is the same polarity or the opposite polarity of the pulse applied to the second electrode contact whenever the third electrode contact is spatially far from the second electrode contact;

continuing to stimulate electrode contacts on the electrode array following the above pattern until a desired number of electrode contacts have been stimulated;

repeating the above stimulation pattern for all of the electrode contacts on the electrode array that are stimulated by a first monophasic pulse of one polarity by stimulating that electrode contact with a second monophasic pulse of an opposite polarity, whereby a selected number of the electrode contacts on the electrode array are stimulated sequentially in accordance with an alterphasic inverting stimulation strategy; and modulating the alterphasic inverting stimulation with sound information.

2. The method of claim 1 wherein the electrode array has sixteen electrode contacts, designated as E1, E2, ... E16, with electrode contact E1 being the most distal electrode contact, and electrode contact E16 being the most proximal electrode contact, and wherein the sequence of applying monophasic pulses to the sixteen electrode contacts, and the polarity of the first monophasic pulses of the alterphasic pulse comprises:

E1(−), E8(+), E3(+), E10(−), E5(−), E12(+), E7(+), E14(−), E9 (−), E16(+), E2(−), E11(+), E4(+), E13(−), E6(−), E15(+), ... ;

wherein the polarity symbol in parenthesis after each electrode contact indicates the polarity of the first pulse of the alterphasic pulse applied to that electrode contact, and wherein a time gap of T1 seconds is inserted between the two monophasic pulses of the alterphasic pulse.

3. The method of claim 2 wherein the time gap of T1 seconds is 1 to 100 µs.

4. The method of claim 1 wherein the alterphasic inverting stimulation strategy reduces power associated with operation of a cochlear implant system.

5. The method of claim 1 wherein the alterphasic inverting stimulation strategy improves the ability of a user to perceive sound, as well as to improve the ability of the user to discern quality of sound.

6. In a multichannel cochlear stimulation system having an electrode array insertable into a human cochlea, and wherein the electrode array has a multiplicity of spaced-apart electrode contacts positioned at or near its distal end, a low power stimulation strategy for use within the cochlear stimulation system comprising:

means for applying an alterphasic inverting stimulation strategy to at least a multiplicity of the multiplicity of electrode contacts on the electrode array, said alterphasic inverting stimulation comprises a multiplicity of cycles on a multiplicity of channels, wherein at least one cycle of the multiplicity of cycles includes alterphasic inverting monophasic pulses occurring within the multiplicity of channels; and means for modulating the stimulation pulses provided by the alterphasic inverting stimulation strategy with sound information.

7. In a multichannel cochlear stimulation system having an electrode array insertable into a human cochlea, and wherein the electrode array has a multiplicity of spaced-apart electrode contacts positioned at or near its distal end, a low power stimulation strategy for use within the cochlear stimulation system comprising:

means for applying an alterphasic inverting stimulation strategy to at least a multiplicity of the multiplicity of electrode contacts on the electrode array; and means for modulating the stimulation pulses provided by the alterphasic inverting stimulation strategy with sound information;

wherein the means for applying an alterphasic inverting stimulation strategy comprises:

means for stimulating a first electrode contact on the electrode array with a monophasic pulse having a first polarity;

means for stimulating a second electrode contact on the electrode array following stimulation of the first electrode contact with a monophasic pulse having a second polarity, wherein the second polarity is the opposite polarity of the pulse applied to the first electrode contact whenever the second electrode contact is spatially near the first electrode contact, and wherein the second polarity is the same polarity or the opposite polarity of the pulse applied to the first electrode contact whenever the second electrode contact is spatially far from the first electrode contact;

means for stimulating a third electrode contact on the electrode array following stimulation of the second electrode contact with a monophasic pulse having a third polarity, wherein the third polarity is the opposite polarity of the pulse applied to the second electrode contact whenever the third electrode contact is spatially near the second electrode contact, and wherein the third polarity is the same polarity or the opposite polarity of the pulse applied to the second electrode contact whenever the third electrode contact is spatially far from the second electrode contact;

means for continuing to stimulate electrode contacts on the electrode array following the above pattern until a desired number of electrode contacts have been stimulated; and means for repeating the above stimulation pattern for all of the electrode contacts on the electrode array that are stimulated by a first monophasic pulse of one polarity by stimulating that electrode contact with a second monophasic pulse of an opposite polarity, whereby a selected number of the electrode contacts on the electrode array are stimulated sequentially in accordance with the alterphasic inverting stimulation strategy.

8. The alterphasic inverting stimulation strategy of claim 7 further including means for inserting a time gap of T1 seconds between two monophasic pulses of the alterphasic pulse, wherein T1 ranges from 1 to 100 µs.

9. A method of providing a low power stimulation strategy for use within a cochlear stimulation system, said stimulation system including an electrode array insertable into a human cochlea, wherein the electrode array has a multiplicity of spaced-apart electrode contacts positioned at or near its distal end, the method comprising:

applying an alterphasic inverting stimulation to at least a multiplicity of the multiplicity of electrode contacts on the electrode array, said alterphasic inverting stimulation comprises a multiplicity of cycles on a multiplicity of channels, wherein at least one cycle of the multiplicity of cycles includes alterphasic inverting monophasic pulses occurring within the multiplicity of channels; and modulating the stimulation pulses provided by the alterphasic inverting stimulation with sound information.

10. A method of providing a low power stimulation strategy for use within a cochlear stimulation system, said stimulation system including an electrode array insertable into a human cochlea, wherein the electrode array has a multiplicity of spaced-apart electrode contacts positioned at or near its distal end, the method comprising:

applying an alterphasic inverting stimulation to at least a multiplicity of the multiplicity of electrode contacts on the electrode array; and modulating the stimulation pulses provided by the alterphasic inverting stimulation with sound information;

wherein applying the alterphasic inverting stimulation comprises:

stimulating a first electrode contact on the electrode array with a monophasic pulse having a first polarity;

stimulating a second electrode contact on the electrode array following stimulation of the first electrode contact with a monophasic pulse having a second polarity, wherein the second polarity is the opposite polarity of the pulse applied to the first electrode contact whenever the second electrode contact is spatially near the first electrode contact, and wherein the second polarity is the same polarity or the opposite polarity of the pulse applied to the first electrode contact whenever the second electrode contact is spatially far from the first electrode contact;

stimulating a third electrode contact on the electrode array following stimulation of the second electrode contact with a monophasic pulse having a third polarity, wherein the third polarity is the opposite polarity of the pulse applied to the second electrode contact whenever the third electrode contact is spatially near the second electrode contact, and wherein the third polarity is the same polarity or the opposite polarity of the pulse applied to the second electrode contact whenever the third electrode contact is spatially far from the second electrode contact;

continuing to stimulate electrode contacts on the electrode array following the above pattern until a desired number of electrode contacts have been stimulated; and repeating the above stimulation pattern for all of the electrode contacts on the electrode array that are stimulated by a first monophasic pulse of one polarity by stimulating that electrode contact with a second monophasic pulse of an opposite polarity, whereby a selected number of the electrode contacts on the electrode array are stimulated sequentially in accordance with the alterphasic inverting stimulation strategy.

11. The stimulation strategy of claim 6 wherein the at least one cycle includes a time gap of T1 seconds between two monophasic pulses, wherein T1 ranges from 1 to 100 μs.

12. The method of claim 9 further including inserting a time gap of T1 seconds between two monophasic pulses for the at least one cycle, wherein T1 ranges from 1 to 100 μs.

* * * * *